US009061961B2

(12) United States Patent
Kubanek et al.

(10) Patent No.: US 9,061,961 B2
(45) Date of Patent: *Jun. 23, 2015

(54) METHOD FOR DIRECT AMINATION OF HYDROCARBONS TO FORM AMINO HYDROCARBONS WITH THE ELECTROCHEMICAL SEPARATION OF HYDROCARBON

(75) Inventors: Petr Kubanek, Mannheim (DE); Alexander Panchenko, Ludwigshafen (DE); Andreas Fischer, Heppenheim (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 555 days.

This patent is subject to a terminal disclaimer.

(21) Appl. No.: 13/383,321

(22) PCT Filed: Jul. 8, 2010

(86) PCT No.: PCT/EP2010/059771
§ 371 (c)(1),
(2), (4) Date: Jan. 10, 2012

(87) PCT Pub. No.: WO2011/003964
PCT Pub. Date: Jan. 13, 2011

(65) Prior Publication Data
US 2012/0111732 A1    May 10, 2012

(30) Foreign Application Priority Data
Jul. 10, 2009  (EP) .................................. 09165219

(51) Int. Cl.
*C07C 209/02* (2006.01)
*C25B 3/00* (2006.01)

(52) U.S. Cl.
CPC ................. *C07C 209/02* (2013.01); *C25B 3/00* (2013.01)

(58) Field of Classification Search
CPC .......... B01D 53/326; C01B 3/50; C25B 1/02; C07C 209/02
USPC .................................. 205/431, 462, 463, 637
See application file for complete search history.

(56) References Cited

U.S. PATENT DOCUMENTS

| 3,919,155 | A | 11/1975 | Squire | |
|---|---|---|---|---|
| 3,929,889 | A | 12/1975 | Squire | |
| 4,001,260 | A | 1/1977 | Del Pesco | |
| 4,031,106 | A | 6/1977 | Del Pesco | |
| 7,741,522 | B2 | 6/2010 | Van Laar et al. | |
| 7,838,702 | B2 | 11/2010 | Van Laar et al. | |
| 8,487,152 | B2 * | 7/2013 | Coelho Tsou et al. | 585/407 |
| 8,575,411 | B2 * | 11/2013 | Coelho Tsou et al. | 585/407 |
| 8,609,914 | B2 * | 12/2013 | Coelho Tsou et al. | 585/407 |
| 8,729,331 | B2 * | 5/2014 | Coelho Tsou et al. | 585/818 |
| 2006/0054512 | A1 * | 3/2006 | Ballantine et al. | 205/637 |
| 2007/0246374 | A1 * | 10/2007 | Eisman et al. | 205/765 |
| 2009/0203941 | A1 | 8/2009 | Laar et al. | |
| 2009/0292144 | A1 | 11/2009 | Anders et al. | |
| 2010/0274008 | A1 | 10/2010 | Kubanek et al. | |
| 2010/0274009 | A1 | 10/2010 | Kubanek et al. | |
| 2010/0274010 | A1 | 10/2010 | Kubanek et al. | |
| 2010/0274011 | A1 | 10/2010 | Kubanek et al. | |
| 2010/0274055 | A1 | 10/2010 | Kubanek et al. | |
| 2011/0054167 | A1 | 3/2011 | Kubanek et al. | |
| 2011/0108432 | A1 | 5/2011 | Malkowsky et al. | |
| 2011/0124933 | A1 | 5/2011 | Kiesslich et al. | |
| 2011/0303550 | A1 | 12/2011 | Coelho Tsou et al. | |
| 2012/0004482 | A1 | 1/2012 | Tsou et al. | |
| 2012/0012467 | A1 | 1/2012 | Coelho Tsou et al. | |
| 2012/0012471 | A1 | 1/2012 | Coelho Tsou et al. | |
| 2012/0064635 | A1 | 3/2012 | Feitisch et al. | |

FOREIGN PATENT DOCUMENTS

| JP | 2004-307248 A | 11/2004 |
|---|---|---|
| JP | 2005-048247 A | 2/2005 |
| JP | 2005-243603 A | 9/2005 |
| JP | 2005-298307 A | 10/2005 |

(Continued)

OTHER PUBLICATIONS

English translation of the Office Action issued Sep. 17, 2013 in Japanese Patent Application No. 2012-518986.
U.S. Appl. No. 13/383,014, filed Jan. 9, 2012, Kubanek, et al.
U.S. Appl. No. 13/320,384, filed Nov. 14, 2011, Koenigsmann, et al.
U.S. Appl. No. 61/183,251, filed Jun. 2, 2009, Schwab, et al.
U.S. Appl. No. 13/375,805, filed Dec. 2, 2011, Schwab, et al.

(Continued)

*Primary Examiner* — Nicholas A Smith
(74) *Attorney, Agent, or Firm* — Oblon, McClelland, Maier & Neustadt, L.L.P.

(57) ABSTRACT

Process for the direct amination of hydrocarbons to aminohydrocarbons, which comprises the steps:

a) reaction of a feed stream E comprising at least one hydrocarbon and at least one aminating reagent to form a reaction mixture R comprising aminohydrocarbons and hydrogen and b) electrochemical separation of at least part of the hydrogen formed in the reaction from the reaction mixture R by means of a gastight membrane-electrode assembly having at least one selectively proton-conducting membrane and at least one electrode catalyst on each side of the membrane, where at least part of the hydrogen is oxidized to protons over the anode catalyst on the retentate side of the membrane and the protons are, after passing through the membrane, b1) reduced to hydrogen and/or b2) reacted with oxygen from an oxygen-comprising stream O which is brought into contact with the permeate side of the membrane to form water over the cathode catalyst on the permeate side.

20 Claims, No Drawings

(56) References Cited

FOREIGN PATENT DOCUMENTS

| | | |
|---|---|---|
| JP | 2009-506090 A | 2/2009 |
| WO | 99 10311 | 3/1999 |
| WO | 00 09473 | 2/2000 |
| WO | 00 69804 | 11/2000 |
| WO | 2007 025882 | 3/2007 |
| WO | 2007 096297 | 8/2007 |
| WO | 2007 099028 | 9/2007 |
| WO | 2008 009668 | 1/2008 |
| WO | 2009 080515 | 7/2009 |
| WO | 2011 003932 | 1/2011 |
| WO | 2011 003934 | 1/2011 |

OTHER PUBLICATIONS

Darling, et al., "Trennung and Reinigung von Wasserstoff durch Permeation an Membranen aus Palladium-Legierungen", Chemie Ingenieur Technik, Wiley VCH, vol. 1, No. 37, pp. 18-27. (1965).

International Search Report issued on Mar. 17, 2011 in PCT/EP10/059771 filed on Jul. 8, 2010.

* cited by examiner

METHOD FOR DIRECT AMINATION OF HYDROCARBONS TO FORM AMINO HYDROCARBONS WITH THE ELECTROCHEMICAL SEPARATION OF HYDROCARBON

The present invention relates to a process for the direct amination of hydrocarbons by means of an amination reagent to form aminohydrocarbons in the presence of a catalyst, where at least part of the hydrogen formed in the reaction is separated off electrochemically by means of a gastight membrane-electrode assembly.

The commercial preparation of aminohydrocarbons from hydrocarbons is usually carried out in multistage reactions. Thus, in the preparation of aniline from benzene, a benzene derivative such as nitrobenzene, chlorobenzene or phenol is firstly prepared and is subsequently converted into aniline in single-stage or multistage reactions.

Processes for the direct preparation of aminohydrocarbons from the corresponding hydrocarbons are also known. Reactions in which aminohydrocarbons are prepared directly from the corresponding hydrocarbons are referred to as direct amination. Wibaut for the first time described the heterogeneous catalyzed direct amination of benzene in 1917 (Berichte 1917, 50, 541-546).

In direct amination, the conversion of the hydrocarbon used into the corresponding aminohydrocarbon takes place with liberation of hydrogen. In the direct amination of benzene to aniline, 1 mol of aniline and 1 mol of hydrogen are formed from 1 mol of benzene and 1 mol of ammonia. The direct amination of benzene to aniline is limited by the position of the thermodynamic equilibrium. The equilibrium conversion at temperatures of 350° C. is about 0.5 mol % based on benzene.

Owing to the low equilibrium conversion, a shift in the position of the thermodynamic equilibrium to the side of the aminohydrocarbons is necessary for the direct amination to be carried out economically. This shift can be achieved by removal of hydrogen from the reaction mixture of the direct amination.

One possibility is to remove hydrogen formed in the direct amination directly from the reaction zone.

A further possibility is to separate off part of the hydrogen from the reaction mixture of the direct amination, which comprises aminohydrocarbon, unreacted starting materials and hydrogen, and reuse the unreacted starting materials in the direct amination reaction. It is necessary to separate off the hydrogen from the reaction mixture since otherwise the thermodynamic equilibrium is shifted by the hydrogen in the direction of the starting materials, as a result of which the yield of aminohydrocarbon becomes even lower in the renewed direct amination.

A number of methods have been described for removing the hydrogen from the reaction mixture.

WO 2007/096297 and WO 2000/69804 describe a process for the direct amination of aromatic hydrocarbons to the corresponding aminohydrocarbons, with the hydrogen formed being removed from the reaction mixture by oxidation over reducible metal oxides. These processes have the disadvantage that the reducible metal oxides have to be regenerated by means of oxygen after some time. This means costly interruptions of the process since the direct amination of the hydrocarbons and the regeneration of the reducible metal oxides usually do not proceed under the same conditions. To regenerate the catalyst, the reactor therefore usually has to be depressurized, flushed and made inert.

A further undesirable secondary reaction which occurs in the direct amination of hydrocarbons to aminohydrocarbons is the decomposition of ammonia to form hydrogen. This decomposition is disadvantageous since, firstly, the starting material ammonia is lost and, secondly, the hydrogen formed in the decomposition leads to a further unfavorable shift in the position of the equilibrium in the direction of the starting materials. In the case of the catalysts described in WO 2007/096297 and WO 2000/69804, the undesirable decomposition of ammonia increases with increasing degree of reduction of the metal oxides, so that the position of the equilibrium is shifted ever further in the direction of the starting materials with increasing degree of reduction.

WO 2007/099028 describes a direct amination process for converting aromatic hydrocarbons into the corresponding aminohydrocarbons, in which the heterogeneously catalyzed direct amination is carried out in a first step and the hydrogen formed in the first step is reacted with an oxidant such as air, oxygen, CO, $CO_2$, NO and/or $N_2O$ in a second step. The use of oxidants such as oxygen leads to oxidation of ammonia and formation of further by-products. This leads to higher materials costs and to additional work-up steps, as a result of which the economics of the process is adversely affected.

WO 2008/009668 likewise describes a process for the direct amination of aromatic hydrocarbons. Removal of the hydrogen from the reaction mixture is in this case achieved by carrying out the direct amination with addition of compounds which react with the hydrogen formed in the direct amination. As compounds added to the direct amination, nitrobenzene and carbon monoxide are described by way of example. In this process, too, the above-described disadvantages occur.

WO 2007/025882 describes the direct amination of aromatic hydrocarbons to the corresponding aminohydrocarbons, with hydrogen being separated off physically from the reaction mixture. The separation is in this case effected by means of a selectively hydrogen-permeable membrane, i.e. hydrogen migrates as $H_2$ molecules through the membrane. As membrane materials, preference is given to using palladium and palladium alloys. The diffusion rate in this process depends on the difference in the partial pressure of hydrogen between retentate side and permeate side of the membrane. To achieve higher diffusion rates, it is necessary to work at higher pressure differences which place severe demands on the mechanical stability of the membrane. In addition, Basile, Top. Catal. (2008), 51, 107-122, states that temperatures above 300° C. are necessary for achieving a sufficiently high diffusion rate. Furthermore, appropriate apparatuses for compressing and expanding the gas mixture have to be present in order to generate the pressure differences. In addition, a certain proportion of the hydrogen always remains in the retentate for thermodynamic reasons. This has an adverse effect on the position of the thermodynamic equilibrium.

It is therefore an object of the present invention to provide a process for the direct amination of hydrocarbons to aminohydrocarbons, in which hydrogen is separated off very effectively from the reaction mixture and the abovementioned disadvantages of the direct amination processes known from the prior art are avoided. In addition, the process should make it possible for the position of the thermodynamic equilibrium to be shifted to the side of the aminohydrocarbons. The hydrocarbons used should, like the by-products obtained in the reaction, be utilized efficiently. The process should have a very favorable energy balance and a very low outlay in terms of apparatus.

The object is achieved according to the invention by a process for the direct amination of hydrocarbons to aminohydrocarbons, which comprises the steps:

a) reaction of a feed stream E comprising at least one hydrocarbon and at least one aminating reagent to form a reaction mixture R comprising aminohydrocarbons and hydrogen and
b) electrochemical separation of at least part of the hydrogen formed in the reaction from the reaction mixture R by means of a gastight membrane-electrode assembly having at least one selectively proton-conducting membrane and at least one electrode catalyst on each side of the membrane, where at least part of the hydrogen is oxidized to protons over the anode catalyst on the retentate side of the membrane and the protons are, after passing through the membrane,
b1) reduced to hydrogen and/or
b2) reacted with oxygen from an oxygen-comprising stream O which is brought into contact with the permeate side of the membrane to form water
over the cathode catalyst on the permeate side.

Compared to the known processes in which the hydrogen is removed by means of reducible metal oxides, the process of the invention has the advantage that complicated and costly interruptions to the direct amination process are avoided and that the process can be operated continuously over a longer period of time. In addition, unlike known processes in which gaseous oxidants such as air, oxygen, $CO$, $CO_2$, $NO$ or $N_2O$ or compounds such as nitrobenzene are used, the process of the invention does without removal of the by-products formed as a result of the addition of the oxidants, which is complicated in terms of apparatus and costly.

The process of the invention has the advantage over the processes described in the prior art that the hydrogen is separated electrochemically from the hydrogen-comprising reaction mixture R. The driving force for the removal of hydrogen is based either on a potential difference between the two sides of the membrane which is selectively permeable to protons (alternative b1)) or on the negative free enthalpy of the reaction of hydrogen and oxygen to form water (alternative b2)).

The use of selectively proton-conducting membranes enables the process to be operated largely independently of pressure differences as are necessary when using membranes which are selectively permeable to hydrogen molecules. As a result, the removal of hydrogen can be carried out at lower pressures and pressure differences and a pressure difference applied externally is preferably omitted entirely. This significantly reduces the mechanical stress on the membrane, which leads to an increase in its long-term stability. In addition, the choice of materials possible for the membrane is widened.

The electrochemical removal of hydrogen is significantly more effective than the removal of hydrogen by means of a hydrogen-selective membrane. The membrane area required can therefore be made smaller or, at the same membrane area, significantly more hydrogen can be separated from the reaction mixture. The amount of hydrogen remaining in the reaction mixture after separation is then significantly less than in the separation by means of a hydrogen-selective membrane.

If the process of the invention is operated according to alternative b1), very pure hydrogen is obtained in the process. Very pure hydrogen can be used in many further reactions or processes which are sensitive to impurities and is thus a valuable by-product.

If the process of the invention is operated according to alternative b2), electric energy and heat are liberated in the process. This energy can be utilized for operating the process of the invention. The energy balance of the process of the invention is improved thereby.

Depending on the mode of operation, the user can thus control whether more or exclusively hydrogen or more or exclusively electric energy and heat is obtained in the process; in particular, the electric energy required for removal of the hydrogen according to alternative b1) can be provided by the simultaneous removal of hydrogen according to alternative b2).

The invention is described comprehensively below.

Hydrocarbons:

According to the invention, the feed stream E comprises at least one hydrocarbon. Suitable hydrocarbons which can be used in the process of the invention are, for example, hydrocarbons such as aromatic hydrocarbons, aliphatic hydrocarbons and cycloaliphatic hydrocarbons which may be substituted in any way and can have heteroatoms and double or triple bonds within their chain or their ring or rings. Preference is given to using aromatic hydrocarbons and heteroaromatic hydrocarbons in the amination process of the invention.

Suitable aromatic hydrocarbons are, for example, unsaturated cyclic hydrocarbons which have one or more rings and comprise exclusively aromatic C—H bonds. Preferred aromatic hydrocarbons have one or more 5- and/or 6-membered rings.

For the purposes of the present invention, heteroaromatic hydrocarbons are aromatic hydrocarbons in which one or more of the carbon atoms of the aromatic ring has/have been replaced by a heteroatom selected from among N, O and S.

The aromatic hydrocarbons or the heteroaromatic hydrocarbons can be substituted or unsubstituted. For the purposes of the present invention, substituted aromatic or heteroaromatic hydrocarbons are compounds in which one or more hydrogen atoms bound to a carbon atom and/or heteroatom of the aromatic ring has/have been replaced by another radical. Suitable radicals are, for example, substituted or unsubstituted alkyl, alkenyl, alkynyl, heteroalkyl, heteroalkenyl, heteroalkynyl, cycloalkyl and/or cycloalkynyl radicals; halogen, hydroxy, alkoxy, aryloxy, amino, amido, thio and phosphino. Preferred radicals on the aromatic or heteroaromatic hydrocarbons are selected from among $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido, where the notation $C_{1-6}$- refers to the number of carbon atoms in the main chain of the alkyl radical, the alkenyl radical or the alkynyl radical and the notation $C_{3-8}$- refers to the number of carbon atoms in the cycloalkyl or cycloalkenyl ring. Furthermore, the substituents (radicals) on the substituted aromatic or heteroaromatic hydrocarbon can in turn have further substituents.

The number of substituents (radicals) on the aromatic or heteroaromatic hydrocarbon can be chosen at will. However, in a preferred embodiment, the aromatic or heteroaromatic hydrocarbon has at least one hydrogen atom which is bound directly to a carbon atom or a heteroatom of the aromatic or heteroaromatic ring. Thus, a 6-membered ring preferably has 5 or fewer substituents (radicals) and a 5-membered ring preferably has 4 or fewer substituents (radicals). A 6-membered aromatic or heteroaromatic ring particularly preferably bears 4 or fewer substituents, very particularly preferably 3 or fewer substituents (radicals). A 5-membered aromatic or heteroaromatic ring preferably bears 3 or fewer substituents (radicals), particularly preferably 2 or fewer substituents (radicals).

In a particularly preferred embodiment of the process of the invention, an aromatic or heteroaromatic hydrocarbon of the general formula $$(A)-(B)_n$$

where the symbols have the following meanings:

A is, independently, aryl or heteroaryl and is preferably selected from among phenyl, biphenyl, benzyl, dibenzyl, naphthyl, anthracene, pyridyl and quinoline;

n is from 0 to 5, preferably from 0 to 4, in particular when A is a 6-membered aryl or heteroaryl ring; when A is a 5-membered aryl or heteroaryl ring, n is preferably from 0 to 4; regardless of the ring size, n is particularly preferably from 0 to 3, very particularly preferably from 0 to 2 and in particular from 0 to 1; the other carbon atoms or heteroatoms of A which do not bear any substituents B bear hydrogen atoms or, if appropriate, no substituent;

the radicals B are selected independently from the group consisting of alkyl, alkenyl, alkynyl, substituted alkyl, substituted alkenyl, substituted alkynyl, heteroalkyl, substituted heteroalkyl, heteroalkenyl, substituted heteroalkenyl, heteroalkynyl, substituted heteroalkynyl, cycloalkyl, cycloalkenyl, substituted cycloalkyl, substituted cycloalkenyl, halogen, hydroxy, alkoxy, aryloxy, carbonyl, amino, amido, thio and phosphino; with preference being given to the radicals B being selected independently from among $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido, is used The expression independently means that when n is 2 or more, the substituents B can be identical or different radicals from the groups mentioned.

For the purposes of the present patent application, the term alkyl refers to branched or unbranched, saturated acyclic hydrocarbon radicals. Preference is given to using alkyl radicals having from 1 to 20 carbon atoms, particularly preferably from 1 to 6 carbon atoms and in particular from 1 to 4 carbon atoms. Examples of suitable alkyl radicals are methyl, ethyl, n-propyl, i-propyl, n-butyl, t-butyl and i-butyl.

For the purposes of the present patent application, the term alkynyl refers to branched or unbranched acyclic hydrocarbon radicals having at least one carbon-carbon double bond. The alkenyl radicals preferably have from 2 to 20 carbon atoms, particularly preferably from 2 to 6 carbon atoms and in particular 2 or 3 carbon atoms. Suitable alkenyl radicals are, for example, vinyl and 2-propenyl.

For the purposes of the present patent application, the term alkenyl refers to branched or unbranched acyclic hydrocarbon radicals having at least one carbon-carbon triple bond. The alkynyl radicals preferably have from 2 to 20 carbon atoms, particularly preferably from 1 to 6 carbon atoms and in particular 2 or 3 carbon atoms. Examples of suitable alkynyl radicals are ethynyl and 2-propynyl.

Substituted alkyl, substituted alkenyl and substituted alkynyl radicals are alkyl, alkenyl and alkynyl radicals in which one or more hydrogen atoms bound to a carbon atom of these radicals have been replaced by another group. Examples of such other groups are halogen, aryl, substituted aryl, cycloalkyl, cycloalkenyl, substituted cycloalkyl, substituted cycloalkenyl and combinations thereof. Examples of suitable substituted alkyl radicals are benzyl and trifluoromethyl.

The terms heteroalkyl, heteroalkenyl and heteroalkynyl refer to alkyl, alkenyl and alkynyl radicals in which one or more of the carbon atoms in the carbon chain have been replaced by a heteroatom selected from among N, O and S. The bond between the heteroatom and a further carbon atom can be saturated or unsaturated.

For the purposes of the present patent application, the term cycloalkyl refers to saturated cyclic nonaromatic hydrocarbon radicals which are made up of a single ring or a plurality of fused rings. The cycloalkyl radicals preferably have from 3 to 8 carbon atoms and particularly preferably from 3 to 6 carbon atoms. Suitable cycloalkyl radicals are, for example, cyclopropyl, cyclopentyl, cyclohexyl, cyclooctanyl and bicyclooctyl.

For the purposes of the present patent application, the term cycloalkenyl refers to partially unsaturated, cyclic nonaromatic hydrocarbon radicals which have a single ring or a plurality of fused rings. The cycloalkenyl radicals preferably have from 3 to 8 carbon atoms and particularly preferably 5 to 6 carbon atoms. Suitable cycloalkenyl radicals are, for example, cyclopentenyl, cyclohexenyl and cyclooctenyl.

Substituted cyacloalkyl radicals and substituted cycloalkenyl radicals are cycloalkyl and cycloalkenyl radicals in which one or more hydrogen atoms of a carbon atom of the carbon ring have been replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, an aliphatic heterocyclic radical, a substituted aliphatic heterocyclic radical, heteroaryl, substituted heteroaryl, alkoxy, aryloxy, boryl, phosphino, amino, silyl, thio, seleno and combinations thereof. Examples of substituted cycloalkyl and cycloalkenyl radicals are 4-dimethylaminocyclohexyl and 4,5-dibromocyclohept-4-enyl.

For the purposes of the present patent application, the term aryl refers to aromatic radicals which have a single aromatic ring or a plurality of aromatic rings which are fused, joined via a covalent bond or joined via a linking unit such as a methylene or ethylene unit. Such linking units can also be carbonyl units as in benzophenone or oxygen units as in diphenyl ether or nitrogen units as in diphenylamine. The aryl radicals preferably have from 6 to 20 carbon atoms, particularly preferably from 6 to 8 carbon atoms and very particularly preferably 6 carbon atoms. Examples of aromatic rings are phenyl, naphthyl, biphenyl, diphenyl ether, diphenylamine and benzophenone.

Substituted aryl radicals are aryl radicals in which one or more hydrogen atoms bound to carbon atoms of the aryl radical have been replaced by one or more groups such as alkyl, alkenyl, alkynyl, substituted alkyl, substituted alkenyl, substituted alkynyl, cycloalkyl, cycloalkenyl, substituted cycloalkyl, substituted cycloalkenyl, heterocyclo, substituted heterocyclo, halogen, halogen-substituted alkyl (e.g. $CF_3$), hydroxy, amino, phosphino, alkoxy or thio. In addition, one or more hydrogen atoms bound to carbon atoms of the aryl radical can be replaced by one or more groups such as saturated and/or unsaturated cyclic hydrocarbons which may be fused to the aromatic ring or to the aromatic rings or can be joined by a bond or linked to one via a suitable group. Suitable groups are those described above.

For the purposes of the present patent application, the term heteroaryl refers to the abovementioned aryl compounds in which one or more carbon atoms of the radical have been replaced by a heteroatom, e.g. N, O or S.

For the purposes of the present patent application, the term heterocyclo refers to a saturated, partially unsaturated or unsaturated cyclic radical in which one or more carbon atoms of the radical have been replaced by a heteroatom such as N, O or S. Examples of heterocyclo radicals are piperazinyl, morpholinyl, tetrahydropyranyl, tetrahydrofuranyl, piperidinyl, pyrrolidinyl, oxazolinyl, pyridyl, pyrazyl, pyridazyl, pyrimidyl.

Substituted heterocyclo radicals are heterocyclo radicals in which one or more hydrogen atoms bound to one of the ring atoms have been replaced by one or more groups such as halogen, alkyl, substituted alkyl, aryl, substituted aryl, heteroaryl, substituted heteroaryl, alkoxy, aryloxy, boryl, phosphino, amino, silyl, thio, seleno.

For the purposes of the present invention, alkoxy radicals are radicals of the general formula $-OZ^1$, where $Z^1$ is selected from among alkyl, substituted alkyl, cycloalkyl, substituted cycloalkyl, heterocycloalkyl, substituted heterocycloalkyl and silyl. Suitable alkoxy radicals are, for example, methoxy, ethoxy, benzyloxy and t-butoxy.

For the purposes of the present invention, the term aryloxy refers to radicals of the general formula —$OZ^2$, where $Z^2$ is selected from among aryl, substituted aryl, heteroaryl, substituted heteroaryl and combinations thereof. Suitable aryloxy radicals and heteroaryloxy radicals are phenoxy, substituted phenoxy, 2-pyridinoxy and 8-quinolinoxy.

For the purposes of the present invention, amino radicals are radicals of the general formula —$NZ^3Z^4$, where $Z^3$ and $Z^4$ are selected independently from among hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy and silyl.

Aromatic and heteroaromatic hydrocarbons which are preferably used in the amination process of the invention are benzene, naphthalene, diphenylmethane, anthracene, toluene, xylene, phenol and aniline and also pyridine, pyrazine, pyridazine, pyrimidine and quinoline.

In a preferred embodiment, at least one hydrocarbon from the group consisting of benzene, naphthalene, diphenylmethane, anthracene, toluene, xylene, phenol and aniline and also pyridine, pyrazine, pyridazine, pyrimidine and quinoline is accordingly used.

It is also possible to use mixtures of the aromatic or heteroaromatic hydrocarbons mentioned. Particular preference is given to using at least one aromatic hydrocarbon from the group consisting of benzene, naphthalene, anthracene, toluene, xylene, phenol and aniline, very particularly preferably benzene, toluene and naphthalene.

Very particular preference is given to using benzene in the process of the invention.

As aliphatic hydrocarbon, methane is very particularly preferred for use in the process of the invention.

Aminating Reagent:

According to the invention, the feed stream E comprises at least one aminating reagent. Suitable aminating reagents are ones by means of which at least one amino group is introduced into the hydrocarbon used for the direct amination. Examples of preferred aminating reagents are ammonia, primary and secondary amines and compounds which eliminate ammonia under the reaction conditions. It is also possible to use mixtures of two or more of the abovementioned aminating reagents.

A very particularly preferred aminating reagent is ammonia.

Aminohydrocarbons:

In the process of the invention, a feed stream E comprising at least one hydrocarbon and at least one aminating reagent is reacted to form a reaction mixture R comprising at least one aminohydrocarbon and hydrogen. Here, at least one aminohydrocarbon which corresponds to the hydrocarbon used and comprises at least one more amino group than the hydrocarbon used is obtained. For the purposes of the present invention, an aminohydrocarbon is accordingly the reaction product of the hydrocarbons used in the process with the aminating reagent. Here, at least one amino group is transferred from the aminating reagent to the hydrocarbon. In a preferred embodiment, from 1 to 6 amino groups, in a particularly preferred embodiment from 1 to 3 amino groups, very particularly preferably 1 or 2 amino groups and in particular 1 amino group, are/is transferred to the hydrocarbon. The number of amino groups transferred can be controlled by means of the molar ratio of aminating reagent to hydrocarbon to be aminated and by means of the reaction temperature.

The ratio of aminating reagent to hydrocarbon is typically from 0.5 to 9, preferably from 1 to 5, particularly preferably from 1.5 to 3.

When the process of the invention is carried out using benzene as hydrocarbon and ammonia as aminating reagent in a molar ratio in the range from 1 to 9, aniline is obtained as aminohydrocarbon.

When the process of the invention is carried out using toluene as hydrocarbon and ammonia as aminating reagent in a molar ratio in the range from 1 to 9, toluenediamine is obtained as aminohydrocarbon.

When the process of the invention is carried out using methane as hydrocarbon and ammonia as aminating reagent in a molar ratio in the range from 1 to 9, methylamine, dimethylamine or trimethylamine or a mixture of two or more of the abovementioned amines is obtained as aminohydrocarbon.

In a particular embodiment, benzene is reacted with ammonia to form aniline. In a further preferred embodiment, toluene is reacted with ammonia to form toluenediamine.

Catalysts:

The direct amination is carried out in the presence of at least one catalyst.

Suitable catalysts are in principle all known amination catalysts. It is possible to use the catalysts known for the direct amination of hydrocarbons, in particular those for the direct amination of benzene by means of ammonia to form aniline, as catalysts. Such catalysts are described in the patent literature, for example in WO 2007/099028, WO 2007/096297, WO 2000/69804, WO 2008/009668, WO 2007/025882, U.S. Pat. No. 3,919,155, U.S. Pat. No. 3,929,889, U.S. Pat. No. 4,001,260, U.S. Pat. No. 4,031,106 and WO 99/10311. Since the removal of the hydrogen in the process of the invention is carried out electrochemically and not by chemical transformation in the reaction system, it is also possible to use catalysts which have no components which are reactive toward hydrogen.

As catalysts, it is possible to use, for example, customary metal catalysts based on nickel, iron, cobalt, copper, noble metals or alloys of these metals. Preferred noble metals (NM) are Ru, Rh, Pd, Ag, Ir, Pt and Au. In a particular embodiment, the noble metals Ru and Rh are not used alone but instead are used in an alloy with one or more other transition metals such as Co, Cu, Fe and nickel. Examples of suitable catalysts are supported NiCuNM; CoCuNM; NiCoCuNM, NiMoNM, NiCrNM, NiReNM, CoMoNM, CoCrNM, CoReNM, FeCuNM, FeCoCuNM, FeMoNM, FeReNM alloys. Here, NM is a noble metal, preferably Pt, Pd, Ag, Ir, particularly preferably Ag and/or Ir. More particular preference is given to NiCuNM, where NM is selected from among Pt, Pd, Ag and Ir.

In one embodiment, the electrocatalyst (electrode) used on the retentate side simultaneously serves as catalyst for the conversion of hydrocarbon into aminohydrocarbon (amination catalyst). In a further embodiment, the amination catalyst can be applied directly to the electrocatalyst. In this case, the hydrogen liberated in the reaction is conveyed away directly from the catalyst surface of the amination catalyst by the proton-conducting membrane.

The catalyst can be used in a generally customary form, for example as powder or, for use in a fixed bed, in the form of extrudates, spheres, pellets or rings. The catalytically active constituents can be present on a support material. Possible support materials are, for example, inorganic oxides such as $ZrO_2$, $SiO_2$, $Al_2O_3$, MgO, $TiO_2$, $B_2O_3$, CaO, ZnO, BaO, $ThO_2$, $CeO_2$, $Y_2O_3$ and mixtures of these oxides, e.g. magnesium-aluminum oxide, preferably $TiO_2$, $ZrO_2$, $Al_2O_3$, magnesium-aluminum-oxide and $SiO_2$. Particular preference is given to $Al_2O_3$, $ZrO_2$ and magnesium-aluminum-oxide. For the purposes of the present invention, $ZrO_2$ can be either pure $ZrO_2$ or the normal Hf-comprising $ZrO_2$.

The catalysts which are preferably used in the process of the invention can be regenerated, e.g. by passing a reductive atmosphere over the catalyst or passing firstly an oxidative atmosphere and subsequently a reductive atmosphere over or through the catalyst bed. As reductive atmosphere, preference is given to using an $H_2$ atmosphere.

Reaction Conditions for Direct Amination:

The direct amination can be carried out under oxidative or nonoxidative conditions. The direct amination can also be carried out under catalytic or noncatalytic conditions.

In a preferred embodiment, the direct amination takes place in the presence of a catalyst under nonoxidative conditions.

For the purposes of the present invention, nonoxidative in relation to direct amination means that the concentration of oxidants such as oxygen or nitrogen oxides in the starting materials used (feed stream E) is below 5% by weight, preferably below 1% by weight, particularly preferably below 0.1% by weight (in each case based on the total weight of the feed stream E). For the purposes of the present invention, the feed stream E is the stream which is fed into the reactor and comprises at least one hydrocarbon and at least one aminating reagent. The feed stream E is very particularly preferably free of oxygen. Particular preference is likewise given to a concentration of oxidant in the feed stream E which is equal to or lower than the concentration of oxidant in the source from which the hydrocarbons and aminating reagents used originate.

The reaction conditions in the direct amination process of the invention are dependent, inter alia, on the hydrocarbon to be aminated and the catalyst used.

The direct amination is generally carried out at temperatures of from 20 to 800° C., preferably from 50 to 700° C., particularly preferably from 70 to 350° C.

The reaction pressure in the direct amination is preferably from 0.5 to 40 bar, preferably from 1 to 6 bar, particularly preferably from 1 to 3 bar, in particular atmospheric pressure.

The residence time in batch operation of the amination process of the invention is generally from 15 minutes to 8 hours, preferably from 15 minutes to 4 hours, particularly preferably from 15 minutes to 1 hour. In the case of a continuous process, the residence time is generally from 0.1 second to 20 minutes, preferably from 0.5 second to 10 minutes. In the case of the preferred continuous operation, "residence time" in this context means the residence time of the feed stream E over the catalyst, in the case of fixed-bed catalysts thus the residence time in the catalyst bed, in the case of fluidized-bed reactors in the synthesis section of the reactor (part of the reactor where the catalyst is localized).

The relative amount of the hydrocarbon used and the aminating reagent is dependent on the amination reaction carried out and the reaction conditions. In general, at least stoichiometric amounts of the hydrocarbon and of the aminating reagent are used. Preference is given to using one of the reactants in a stoichiometric excess in order to achieve a shift in the equilibrium to the side of the desired product and thus a higher conversion. The aminating reagent is preferably used in a stoichiometric excess over the hydrocarbon. The ratio of aminating reagent to hydrocarbon is from 0.5 to 9, preferably from 1 to 5, particularly preferably from 1.5 to 3.

Removal of Hydrogen:

In the process of the invention, at least part of the hydrogen comprised in the reaction mixture R is separated off electrochemically in step b). For the purposes of the invention, the reaction mixture R is the mixture which is formed by chemical reaction of at least one hydrocarbon with at least one aminating reagent. The reaction mixture therefore usually comprises the corresponding aminohydrocarbon(s) and hydrogen as reaction products. The reaction mixture R may additionally comprise unreacted starting materials. The hydrogen is separated off by means of a gastight membrane-electrode assembly, with the hydrogen to be separated off being transported in the form of protons through the membrane.

The electrodes together with the membrane arranged in between are referred to as membrane-electrode assembly (MEA). The reaction mixture R is passed along one side of the membrane. This side will hereinafter be referred to as the retentate side. The other side of the membrane will hereinafter be referred to as permeate side. According to the invention, the MEA has at least one selectively proton-conducting membrane. The membrane has at least one electrode catalyst on each side, with, for the purposes of the present description, the electrode catalyst present on the retentate side being referred to as anode catalyst and the electrode catalyst present on the permeate side being referred to as cathode catalyst. On the retentate side, the hydrogen is oxidized to protons over the anode catalyst, these pass through the membrane and on the permeate side are, according to alternative b1) reduced to hydrogen over the cathode catalyst and/or, according to alternative b2), converted into water over the cathode catalyst.

In alternative b1), electric energy has to be expended for the transport of the protons through the membrane and this electric energy is supplied by applying a DC potential to the two sides of the membrane by means of electrodes.

The removal of the hydrogen according to alternative b1) is accordingly brought about by establishment of a potential difference between the two sides of the membrane by application of a potential. The removal is carried out at potentials of from 0.05 to 2000 mV, preferably from 100 to 900 mV, particularly preferably from 100 to 800 mV, measured relative to a hydrogen reference electrode (HRE).

In alternative b2), an oxygen-comprising stream O is conveyed along the membrane on the permeate side. According to alternative b2), the protons react with the oxygen to form water over the cathode catalyst on the permeate side. The driving force is the reduction of oxygen. In the overall reaction, energy is liberated in the form of heat and, by connection of a load, in the form of electric current.

The removal of the hydrogen in step b) of the process of the invention can, both in variant b1) and in variant b2), be carried out at temperatures of from 20 to 800° C., preferably from 50 to 700° C., particularly preferably from 70 to 350° C. When MEAs based on polybenzimidazole and phosphoric acid are used, the separation is preferably carried out at from 130 to 200° C. When ceramic membranes, e.g. membranes based on ammonium polyphosphate, are used, temperatures of from 250 to 350° C. can be employed.

The removal of the hydrogen in step b) of the process of the invention is preferably carried out at pressures of from 0.5 to 10 bar, preferably from 1 to 6 bar, particularly preferably from 1 to 3 bar, in particular at atmospheric pressure. In a preferred embodiment of the invention, the pressure difference between the retentate side and the permeate side of the membrane is less than 1 bar, preferably less than 0.5 bar; there is particularly preferably no pressure difference.

According to the invention, at least part of the hydrogen formed in the direct amination is separated off. Preference is given to separating off at least 30%, particularly preferably at least 50%, particularly preferably at least 70% and very particularly preferably at least 95%, in particular at least 98%.

The hydrogen obtained on the permeate side according to alternative b1) comprises not more than 5 mol %, preferably not more than 2 mol % and particularly preferably not more than 1 mol %, of hydrocarbons.

The hydrogen can, depending on the selectively proton-conducting membrane used, comprise up to 30 mol %, preferably up to 10 mol %, particularly preferably up to 2 mol %, of water. The presence of water is necessary for some types of membrane, for example in the case of particular polymer membranes for moistening the polymer membrane.

According to the invention, the electrochemical removal of the hydrogen according to step b) takes place outside the reaction zone in which step a) is carried out.

In a preferred embodiment, the separation of the hydrogen from the reaction mixture R (step b)) is carried out in a reactor equipped with at least one gastight MEA. The separation can in one embodiment be carried out, for example, in a reactor whose exterior walls are formed at least partly by gastight MEAs.

According to the invention, the hydrogen can be separated off according to alternative b1), according to alternative b2) or according to both alternatives. The latter means that at least part of the hydrogen is obtained as hydrogen and at least part of the hydrogen is obtained as water with generation of electric energy. The proportion of the hydrogen comprised in the reaction mixture R which is separated off according to each of the alternatives b1) and b2) can be matched to requirements by the user. In a preferred embodiment of the invention when the hydrogen is separated off according to alternatives b1) and b2), the amount of hydrogen separated off according to alternative b2) is at least such that the power generated is sufficient to cover the energy requirement for the removal of hydrogen according to alternative b1).

If the hydrogen is separated off from the reaction mixture R according to both alternatives b1) and b2), this is preferably carried out physically separately since the protons usually react directly to form hydrogen in the presence of oxygen on the permeate side. The reaction mixture can, for example, be passed in succession firstly along an MEA which is in contact with a stream O on the permeate side so that part of the hydrogen is separated off as water. The reaction mixture R is subsequently passed along an MEA to which a potential is applied so that the hydrogen is separated off as hydrogen. The physical separation between the two alternatives b) and b2) can also be effected by the reaction mixture R being passed between two membranes, for example membranes located opposite one another, of which one is in contact with a stream O on the permeate side and to the other of which a potential is applied. In a preferred embodiment, the MEAs are present in the reactor in which the reaction mixture R is formed and the MEAs particularly preferably form at least part of the physical boundary of the reaction zone in which the reaction leading to the reaction mixture R takes place.

The hydrogen which has been separated off can be dried before further use; this is carried out, in particular, when the separation is effected by means of a polymer membrane which has to be moistened.

Reactors:

In the process of the invention, step a) can be carried out using all types of reactor which are suitable for direct amination reactions.

Suitable reactors are thus tube reactors, fixed-bed reactors, fluidized-bed reactors, moving beds, circulating fluidized beds, salt bath reactors, plate heat exchanger reactors, tray reactors having a plurality of trays with or without heat exchange or offtake/input of substreams between the trays, in possible embodiments as radial-flow or axial-flow reactors, with the reactors suitable for the desired reaction conditions (e.g. temperature, pressure and residence time) being used in each case. The reactors can in each case be used as a single reactor, as a series of individual reactors and/or in the form of two or more parallel reactors. The process of the invention can be carried out as a semicontinuous reaction or continuous reaction. The specific reactor construction and the way in which the reaction is carried out can be varied as a function of the amination process to be carried out, the state of matter of the aromatic hydrocarbon to be aminated, the required reaction times and the nature of the catalyst used. The direct amination process of the invention is preferably carried out in a fixed-bed reactor or fluidized-bed reactor.

Electrode Catalysts:

In step b) of the process of the invention, it is possible to use all electrode catalysts known to those skilled in the art.

The function of electrode catalysts is described, for example, in Journal of Power Sources 177 (2008), 478-484, K. A. Perry, G. A. Eisman, B. C. Benicewicz "Electrochemical hydrogen pumping using a high-temperature polybenzimidazole (PBI) membrane".

To ensure good contact between the membrane and the hydrogen present on the retentate side and good transport of the hydrogen separated off form the permeate side the electrode layers are usually provided with gas diffusion layers. These are, for example, plates having a grid-like surface structure made up of a system of fine channels or layers of porous material such as nonwoven, woven fabric or paper. The totality of gas diffusion layer and electrode layer is generally referred to as gas diffusion electrode (GDE). The gas diffusion layer brings the hydrogen to be separated off close to the membrane and the anode catalyst on the retentate side and on the permeate side aids transport of the hydrogen formed away from the electrode.

Depending on the embodiment of the invention, the anode can simultaneously also serve as anode catalyst and the cathode can simultaneously also serve as cathode catalyst. However, it is also possible to use different materials for the anode and the anode catalyst and/or for the cathode and the cathode catalyst.

In an embodiment of the invention, the anode catalyst can also simultaneously serve as amination catalyst. In this case, the anode catalyst is formed by at least one material from among the abovementioned amination catalysts.

To produce the electrodes, it is possible to use the customary materials known to those skilled in the art, for example Pt, Pd, Cu, Ni, Ru, Co, Cr, Fe, Mn, V, W, tungsten carbide, Mo, molybdenum carbide, Zr, Rh, Ag, Ir, Au, Re, Y, Nb, electrically conductive forms of carbon such as carbon black, graphite and nanotubes and also alloys and mixtures of the abovementioned elements.

The anode and the cathode can be made of the same material or of different materials. The anode catalyst and the cathode catalyst can be selected from among the same materials or from among different materials. Particular preference is given to the anode/cathode combinations Pt/Pt, Pd/Pd, Pt/Pd, Pd/Pt, Pd/Cu, Pd/Ag, Ni/Pt, Ni/Ni and Fe/Fe.

As electrode catalyst material, it is possible to use the customary compounds and elements known to those skilled in the art which can catalyze the dissociation of molecular hydrogen into atomic hydrogen, the oxidation of hydrogen to protons and the reduction of protons to hydrogen. Examples of suitable catalyst materials are Pd, Pt, Cu, Ni, Ru, Fe, Co, Cr, Mn, V, W, tungsten carbide, Mo, molybdenum carbide, Zr, Rh, Ag, Ir, Au, Re, Y, Nb and also alloys and mixtures thereof;

according to the invention, preference is given to Pd, Pt and Ni. The elements and compounds mentioned above as electrode catalyst materials can also be present in supported form, with preference being given to using carbon as support.

In a preferred embodiment of the present invention, electrodes comprising carbon as conductive material are preferably used. Here, the carbon and an electrode catalyst are preferably applied to a porous support such as nonwoven, woven fabric or paper. The carbon can be mixed with the catalyst or the carbon can be applied first followed by the catalyst.

In a further embodiment of the invention, the electrically conductive material used as electrode and the electrode catalyst can be applied directly to the membrane.

Membranes:

The membrane in step b) is preferably configured as a plate or a tube, with the customary membrane arrangements known from the prior art for the separation of gas mixtures, for example tube bundle membranes or plug-in plate membranes, being able to be used.

The MEA used according to the invention is gastight, i.e. it has virtually no porosity through which the gases can pass in atomic or molecular form from one side to the other side of the MEA nor does it have mechanisms by means of which the gases can be transported unselectively through the MEA, for example by absorption, dissolution in the membrane, diffusion and desorption. The impermeability of the membrane-electrode assembly (MEA) can be ensured either by means of a gastight membrane, by means of a gastight electrode or a gastight electrode catalyst or else by a combination thereof. Thus, it is possible to use, for example, a thin metallic foil, for example a Pd, Pd—Ag or Pd—Cu foil, as gastight electrode. Furthermore, the membrane used according to the invention selectively conducts protons, which means, in particular, that it does not conduct electrons.

According to the invention, the membranes can be made of all materials which are known to those skilled in the art and from which selectively proton-conducting membranes can be formed. These include, for example, the materials described by J. W. Phair and S. P. S. Badwal in Ionics (2006) 12, pages 103-115. Selectively proton-conducting membranes as are known from fuel cell technology can also be used according to the invention.

For example, it is possible to use the following ceramic membranes such as particular heteropolyacids such as $H_3Sb_3B_2O_{14} \cdot 10H_2O$, $H_2Ti_4O_9 \cdot 12H_2O$ and $HSbP_2O_8 \cdot 10H_2O$; acid zirconium silicates, phosphates and phosphonates having a sheet structure, e.g. $K_2ZrSi_3O_9$, $K_2ZrSi_3O_9$, alpha-$Zr(HPO_4)_2 \cdot nH_2O$, gamma-$Zr(PO_4)$—$(H_2PO_4) \cdot 2H_2O$, alpha- and gamma-Zr sulfophenylphosphonate or sulfoarylphosphonate; uncoated oxide hydrates such as antimonic acid ($Sb_2O_5 \cdot 2H_2O$), $V_2O_5 \cdot nH_2O$, $ZrO_2 \cdot nH_2O$, $SnO_2 \cdot nH_2O$ and $Ce(HPO_4)_2 \cdot nH_2O$. It is also possible to use oxo acids and salts comprising, for example, sulfate, selenate, phosphate, arsenate, nitrate groups, etc. Oxo anion systems based on phosphates or complex heteropolyacids, e.g. polyphosphate glasses, aluminum polyphosphate, ammonium polyphosphate and polyphosphate compositions such as $NH_4PO_3/(NH_4)_2SiP_4O_{13}$ and $NH_4PO_3/TiP_2O_7$, are particularly useful. It is also possible to use oxidic materials such as brownmillerite, fluorite and phosphates having an apatite structure, pyrochlor minerals and perovskites. It is generally possible to use all proton-conducting materials, including, for example, zeolites, aluminosilicates, $xAl_2O_3(1-x)SiO_2$, $SnP_2O_7$, $Sn_{1-x}In_xP_2O_7$ (x=0.0-0.2).

Perovskites have the basic formula $AB_{1-x}M_xO_{3-y}$, where M is a trivalent rare earth element which serves as dopant and y is the oxygen deficiency in the perovskite oxide lattice. A can, for example, be selected from among Mg, Ca, Sr and Ba. B can be selected, inter alia, from among CeZr and Ti. It is also possible to select different elements independently from the respective groups for A, B and M.

Furthermore, it is possible to use structurally modified glasses such as chalcogenide glasses, PbO—$SiO_2$, BaO—$SiO_2$ and CaO—$SiO_2$.

Further suitable proton-conducting ceramics and oxides are described, for example, in Solid State Ionics 125, (1999), 271-278; Journal of Power Sources 180, (2008), 15-22; Ionics 12, (2006), 103-115; Journal of Power Sources 179 (2008) 92-95; Journal of Power Sources 176 (2008) 122-127 and Electrochemistry Communications 10 (2008) 1005-1007.

Examples of proton-conducting ceramics and oxides are $SrCeO_3$, $BaCeO_3$, Yb:$SrCeO_3$, Nd:$BaCeO_3$, Gd:$BaCeO_3$, Sm:$BaCeO_3$, $BaCaNdO_9$, Y:$BaCeO_3$, Y:$BaZrCeO_3$, Pr-doped Y:$BaCeO_3$, Gd:$BaCeO_3$, $BaCe_{0.9}Y_{0.1}O_{2.95}$ (BYC), $SrCe_{0.95}Yb_{0.05}O_{3-\alpha}$, $BaCe_{0.9}Nd_{0.10}O_{3-\alpha}$, $CaZr_{0.96}In_{0.04}O_{3-\alpha}$, ($\alpha$ denotes the number of oxygen vacancies per formula unit of the oxide of the perovskite type); Sr-doped $La_3P_3O_9$, Sr-doped $LaPO_4$, $BaCe_{0.9}Y_{0.1}O_{3-\alpha}$ (BCY), $BaZr_{0.9}Y_{0.1}O_{3-\alpha}$ (BZY), $Ba_3Ca_{1.18}Nb_{1.82}O_{8.73}$ (BCN18), $(La_{1.95}Ca_{0.05})Zr_2O_{7-\alpha}$, $La_2Ce_2O_7$, $Eu_2Zr_2O_7$, $H_2S/(B_2S_3$ or $Ga_2S_3)/GeS_2$, $SiS_2$, $As_2S_3$ or CsI; $BaCe_{0.8}Gd_{0.2}O_{3-\alpha}$ (BCGO); Gd-doped $BaCeO_3$ such as $BaCe_{0.85}Y_{0.15}O_{3-\alpha}$ (BCY15) and $BaCe_{0.8}Sm_{0.2}O_{3-\alpha}$, $xAl_2O_3(1-x)SiO_2$, $SnP_2O_7$, $Sn_{1-x}In_xP_2O_7$ (x=0.0-0.2).

A further class of materials which are suitable for producing gastight and selectively proton-conducting membranes are polymer membranes. Suitable polymers are sulfonated polyether ether ketones (S-PEEK), sulfonated polybenzimidazoles (S-PBI) and sulfonated fluorohydrocarbon polymers (NAFION®). Furthermore, perfluorinated polysulfonic acids, polymers based on styrene, poly(arylene ethers), polyimides and polyphosphazenes can be used. It is also possible to use polybenzimidazoles based on polybenzimidazole and phosphoric acid, as are marketed, for example, under the name Celtec-P® by BASF SE.

According to the invention, the abovementioned ceramic membranes are preferably used as materials for the selectively proton-conducting membrane.

When polymer membranes are used, they are usually moistened by the presence of from about 0.5 to 30% by volume of water on at least one side of the membrane.

Work-Up of the Product Stream:

The removal of the hydrogen from the reaction mixture R in step b) is effected by means of at least one MEA. After the hydrogen has been separated off from the reaction mixture R, this mixture comprises, in a preferred embodiment, less than 500 ppm, preferably less than 200 ppm and particularly preferably less than 100 ppm, of hydrogen.

Subsequent to the removal of the hydrogen from the reaction mixture R effected by means of at least one MEA, a product stream P is obtained. That comprises the at least one aminohydrocarbon and optionally unreacted starting materials, like hydrocarbons and aminating reagents and optionally non-removed hydrogen. In a preferred embodiment, the product stream P comprises less than 500, preferably less than 200 and particularly less than 100 ppm of hydrogen.

The aminohydrocarbon and/or aminating reagent can be separated off by generally known methods with which those skilled in the art will be familiar, for example by condensation, distillation or extraction. The choice of the pressure and temperature range depends on the physical properties of the compounds to be separated and is known to those skilled in the art.

In one embodiment, the aminohydrocarbons formed are separated off from the reaction mixture between step a) and step b). In a further embodiment, according to the invention the aromatic hydrocarbons formed are separated off from the reaction mixture R after step b). In a further embodiment of the invention, the aromatic hydrocarbons formed are separated off from the product stream P after step b).

In a particularly preferred embodiment of the invention, the reaction mixture R after the aminohydrocarbons and/or the aminating reagent and at least part of the hydrogen have been separated off is recirculated to the process; the reaction mixture R is recirculated either to the feed stream E or directly into the reaction zone of the direct amination.

The invention is illustrated by the following examples without being restricted thereto.

EXAMPLE 1

20 ml of Ni—Cu/$Al_2O_3$ catalyst are installed as a fixed bed in an amination reactor having an internal diameter of 1 cm and a length of 50 cm. 68 g/h of benzene and 44 g/h of ammonia (feed stream E) are subsequently introduced into the amination reactor at a temperature of 350° C. and a pressure of 40 bar. A mixture of benzene, aniline (99.5% of benzene and 0.42% of aniline were found in the liquid output), 3900 ppm of hydrogen, 1100 ppm of nitrogen and ammonia (balance) is obtained as reactor output (reaction mixture R).

The reactor output is conveyed into a downstream reactor (electrochemical cell) having a gastight MEA having an active area of 45 $cm^2$. CeltecP® (polyimidazole/phosphoric acid) from BASF Fuel Cell GmbH is used as membrane of the MEA. As electrodes of the MEA, palladium foils having a thickness of 10 µm are used both for the anode and for the cathode.

The electrochemical cell is operated at 190° C. A potential ($U_A$) of +250 mV is applied to the MEA. The hydrogen is oxidized to protons at the anode on the retentate side, these protons pass through the membrane and are reduced to hydrogen at the cathode.

A major part of the hydrogen comprised is separated off from the reactor output from the amination reactor in the electrochemical cell. The reactor output from the electrochemical cell is fed back into the amination reactor.

EXAMPLE 2

80 l/h of nitrogen and 0.5 l/h of hydrogen (hydrogen concentration: 6200 ppm) were introduced into an electrochemical cell comprising a gastight MEA having an active area of 45 $cm^2$. CeltecP® (polyimidazole/phosphoric acid) from BASF Fuel Cell GmbH is used as membrane of the MEA. As electrodes of the MEA, gas diffusion electrodes ELTA (1 mg/$cm^2$ of platinum) from BASF Fuel Cell GmbH are used both for the anode and for the cathode. The electrochemical cell was operated at 190° C. and a pressure of 1 bar. A potential ($U_A$) of +250 mV was applied to the MEA.

40 ppm of hydrogen and nitrogen (balance) were present in the output from the electrochemical cell. This corresponds to a hydrogen removal of 99.4%.

EXAMPLE 3

In table 1, the effectiveness of the hydrogen removal in example 2 is compared with comparative examples according to the prior art.

TABLE 1

| Example | Material of MEA | Temperature °C. | Potential mV | Hydrogen concentration Input | Hydrogen concentration Output | Pressure difference between retentate side/permeate side bar | Pressure difference between retentate side/permeate side Pa | $H_2$ permeance mol/$m^2 \cdot s \cdot Pa$ |
|---|---|---|---|---|---|---|---|---|
| Example 2 | Pt-GDE/Celtec P | 190 | 250 | 6200 ppm | 40 ppm | 0.00062 | 62 | 1.99E−05 |
| Comparative example 2 | Sol-Gel Si/$AlO_x$ | 200 | | | | | | 5.00E−07 |
| Comparative example 3 | Pd—Ag/a-$Al_2O_3$ | 200-340 | | | | 0.8-2.5 | 100000 | 1.40E−06 |
| Comparative example 4 | Pd | 200 | | | | 0.51 | 51000 | 5.20E−07 |

Comparative example 2 Reference # 55 in *Ind. Eng. Chem. Res.* 2006, 45, 875-881;
Comparative example 3 Reference # 189 in *Top. Catal.* (2008), 51: 107-122;
Comparative example 4 Reference # 158 in *Top. Catal.* (2008), 51: 107-122.

Table 1 shows that the hydrogen flux ($H_2$ permeance mol/$m^2 \times s \times Pa$) through the membrane which can be achieved using the process of the invention is significantly increased compared to the conventional processes described in the prior art.

The invention claimed is:
1. A process for direct amination of a hydrocarbon to an aminohydrocarbon, the process comprising:
    a) reacting a feed stream E comprising a hydrocarbon and an aminating reagent to obtain a reaction mixture R comprising an aminohydrocarbon and hydrogen and
    b) electrochemically separating at least part of the hydrogen from the reaction mixture R with a gastight membrane-electrode assembly, leaving a product stream P,
    wherein the membrane-electrode assembly comprises a selectively proton-conducting membrane having a retentate side and a permeate side, an anode catalyst on the retentate side of the membrane, and a cathode catalyst on the permeate side of the membrane, electrochemically separating at least part of the hydrogen b) comprises oxidizing at least part of the hydrogen to protons over the anode catalyst and passing the protons through the membrane, electrochemically separating at least part of the hydrogen b) further comprises either reducing the protons over the cathode catalyst to obtain hydrogen, or reacting the protons with oxygen from an oxygen-comprising stream O over the cathode catalyst to obtain water.

2. The process of claim 1, further comprising separating the aminohydrocarbon from the reaction mixture R before electrochemically separating at least part of the hydrogen.

3. The process of claim 1, further comprising separating the aminohydrocarbon from the product stream P.

4. The process of claim 1, further comprising:
removing the aminohydrocarbon from the reaction mixture R, removing the aminohydrocarbon from the product stream P, or both, and then
recirculating the product stream P to a direct amination reaction.

5. The process of claim 1, wherein separating hydrogen from the reaction mixture R comprises separating at least 30% of the hydrogen out from the reaction mixture R.

6. The process of claim 1, wherein a temperature of separating hydrogen from the reaction mixture R is from 20 to 800° C.

7. The process of claim 1,
wherein electrochemically separating at least part of the hydrogen b) comprises reducing the protons to hydrogen over the cathode catalyst, and
a potential of electrochemically separating at least part of the hydrogen b) is from 0.05 to 2000 mV.

8. The process claim 1,
wherein electrochemically separating at least part of the hydrogen b) comprises reacting the protons with oxygen from an oxygen-comprising stream O over the cathode catalyst to obtain water, and
the oxygen-comprising stream O comprises at least 15 mol % of oxygen.

9. The process of claim 1, wherein each electrode of the membrane-electrode assembly is a metallic foil.

10. The process of claim 1,
wherein electrochemically separating at least part of the hydrogen b) comprises reacting the protons with oxygen from an oxygen-comprising stream O over the cathode catalyst to obtain water and heat, and
at least part of the heat is fed to a reaction zone where feed stream E reacts to produce reaction mixture R.

11. The process of claim 1, wherein each electrode of the membrane-electrode assembly is a gas diffusion electrode.

12. The process of claim 1,
wherein the selectively proton-conducting membrane comprises at least one membrane selected from the group consisting of a ceramic membrane and a polymer membrane.

13. The process of claim 1,
wherein the hydrocarbon comprises benzene, toluene, methane, or a mixture thereof, and
the aminohydrocarbon comprises aniline, toluenediamine, methylamine, or a mixture thereof.

14. A process for direct amination of a hydrocarbon to an aminohydrocarbon, the process comprising:
a) reacting a feed stream E comprising a hydrocarbon and an aminating reagent to obtain a reaction mixture R comprising an aminohydrocarbon and hydrogen and
b) electrochemically separating at least part of the hydrogen from the reaction mixture R with a gastight membrane-electrode assembly,
wherein the membrane-electrode assembly comprises a selectively proton-conducting membrane having a retentate side and a permeate side, an anode catalyst on the retentate side of the membrane, and a cathode catalyst on the permeate side of the membrane,
electrochemically separating at least part of the hydrogen b) comprises oxidizing at least part of the hydrogen to protons over the anode catalyst and passing the protons through the membrane,
electrochemically separating at least part of the hydrogen b) further comprises both reducing the protons over the cathode catalyst to obtain hydrogen and reacting the protons with oxygen from an oxygen-comprising stream O over the cathode catalyst to obtain water.

15. The process of claim 14, further comprising separating the aminohydrocarbon from the reaction mixture R before electrochemically separating at least part of the hydrogen.

16. The process of claim 14, further comprising separating the aminohydrocarbon from the product stream P.

17. The process of claim 14, further comprising:
removing the aminohydrocarbon from the reaction mixture R, removing the aminohydrocarbon from the product stream P, or both, and then
recirculating the product stream P to a direct amination reaction.

18. The process of claim 14, wherein separating hydrogen from the reaction mixture R comprises separating at least 30% of the hydrogen out from the reaction mixture R.

19. The process of claim 14, wherein reducing the protons over the cathode catalyst to obtain hydrogen comprises reducing the protons with the water obtained from reacting the protons with oxygen.

20. The process of claim 5, wherein separating hydrogen from the reaction mixture R comprises separating at least 50% of the hydrogen out from the reaction mixture R.

* * * * *